US008876705B2

(12) United States Patent
Mathieu et al.

(10) Patent No.: US 8,876,705 B2
(45) Date of Patent: Nov. 4, 2014

(54) MEDICAL ENDOSCOPE COMPRISING A CONSUMABLE INSTRUMENT HAVING A FLUID FLOW CIRCUIT

(75) Inventors: Nicolas Mathieu, Ecully (FR); Olivier Fructus, Nazelles Negron (FR)

(73) Assignee: Axess Vision Technology, Tours (FR)

( * ) Notice: Subject to any disclaimer, the term of this patent is extended or adjusted under 35 U.S.C. 154(b) by 197 days.

(21) Appl. No.: 13/522,377

(22) PCT Filed: Jan. 18, 2011

(86) PCT No.: PCT/FR2011/050084
§ 371 (c)(1),
(2), (4) Date: Jul. 16, 2012

(87) PCT Pub. No.: WO2011/089349
PCT Pub. Date: Jul. 28, 2011

(65) Prior Publication Data
US 2012/0302835 A1    Nov. 29, 2012

(30) Foreign Application Priority Data
Jan. 19, 2010    (FR) ...................................... 10 50333

(51) Int. Cl.
*A61B 1/12* (2006.01)
*A61B 1/015* (2006.01)
*A61B 1/00* (2006.01)

(52) U.S. Cl.
CPC ............. *A61B 1/015* (2013.01); *A61B 1/00105* (2013.01); *A61B 1/00068* (2013.01)
USPC ............ 600/156; 600/131; 600/136; 600/159

(58) Field of Classification Search
CPC ........... A61B 1/00066; A61B 1/00068; A61B 1/00105; A61B 1/00119; A61B 1/00128
USPC .................................. 600/131, 136, 156, 159
See application file for complete search history.

(56) References Cited

U.S. PATENT DOCUMENTS

| 4,403,764 | A | * | 9/1983 | Repplinger ....................... 251/5 |
| 4,519,385 | A | * | 5/1985 | Atkinson et al. .............. 601/161 |
| 4,524,802 | A | * | 6/1985 | Lawrence et al. ............. 137/595 |
| 4,852,551 | A | * | 8/1989 | Opie et al. ..................... 600/121 |
| 5,147,292 | A |   | 9/1992 | Kullas et al. |
| 5,201,908 | A | * | 4/1993 | Jones ............................. 600/123 |

(Continued)

FOREIGN PATENT DOCUMENTS

| EP | 1 493 379 | 1/2005 |
| WO | WO 94/08654 | 4/1994 |
| WO | WO 2008/086497 | 7/2008 |

*Primary Examiner* — Matthew J Kasztejna
(74) *Attorney, Agent, or Firm* — Ladas & Parry LLP

(57) ABSTRACT

The invention provides a medical endoscope including a control handle (2) provided with a control mechanism and that, by means of an attachment system, is temporarily attached to a consumable medical instrument (3) including: at least one flow circuit for a fluid, a portion of which circuit extends along an insertion tube, the fluid circuit including a connector fitting accessible independently from the handle; an actuation system for actuating the head of the insertion tube, which actuation system is driven by the control mechanism after the handle and the consumable medical instrument have been attached together; in accordance with the invention, the control handle (2) and the consumable medical instrument (3) respectively have a first portion and a second portion of a closure device, which portions co-operate with each other in the attached position to close off at least one fluid flow circuit in controlled manner.

9 Claims, 6 Drawing Sheets

(56) References Cited

U.S. PATENT DOCUMENTS

| | | | |
|---|---|---|---|
| 5,203,769 A * | 4/1993 | Clement et al. ............... 604/32 |
| 5,275,151 A * | 1/1994 | Shockey et al. ............ 600/108 |
| 5,344,397 A * | 9/1994 | Heaven et al. ............ 604/95.01 |
| 5,484,402 A | 1/1996 | Saravia et al. |
| 5,531,687 A * | 7/1996 | Snoke et al. ............ 604/95.04 |
| 5,588,634 A * | 12/1996 | Nettekoven ............ 251/9 |
| 5,692,729 A * | 12/1997 | Harhen ............ 251/4 |
| 5,713,850 A | 2/1998 | Heilmann et al. |
| 6,007,531 A * | 12/1999 | Snoke et al. ............ 606/15 |
| 6,017,322 A * | 1/2000 | Snoke et al. ............ 604/95.01 |
| 6,364,853 B1 | 4/2002 | French et al. |
| 6,652,506 B2 * | 11/2003 | Bowe et al. ............ 604/523 |
| 6,666,818 B2 * | 12/2003 | Dhindsa ............ 600/159 |
| 8,052,609 B2 * | 11/2011 | Harhen ............ 600/462 |
| 8,419,623 B2 * | 4/2013 | Garcia et al. ............ 600/136 |
| 2004/0158203 A1 | 8/2004 | Cover et al. |
| 2010/0056867 A1 * | 3/2010 | Labombard et al. ............ 600/121 |

* cited by examiner

MEDICAL ENDOSCOPE COMPRISING A CONSUMABLE INSTRUMENT HAVING A FLUID FLOW CIRCUIT

This application is a 371 of PCT/FR2011/050084, filed on Jan. 18, 2011, which claims priority to French patent application number 10 50333, filed Jan. 19, 2010, which is incorporated herein by reference.

The present invention relates to the technical field of medical equipment in general, and it relates more particularly to a medical endoscope in the general meaning of the term, making it possible to access the inside of an organ or body, such as a cavity or a duct, for example.

The present invention relates more precisely but not exclusively to a medical endoscope for single use including an actuation support such as a handle that is designed to be re-used while the medical instrument that comes into contact with human tissue or organs is for single use, or indeed for use more than once after it has been decontaminated.

The invention applies particularly advantageously to making it possible to access the inside surface of a hollow organ, of a cavity, or of a natural or artificial passage in the human body with a view to performing various operations for therapeutic, surgical, or diagnostic purposes.

The endoscope of the invention is used for diagnostic, therapeutic or surgical purposes for inspecting any of the internal portions of the human body that are accessible via natural or artificial approaches. For example, the endoscope of the invention may be used in the following fields: urinary tracts; of gastrointestinal tracts; the respiratory system; the cardiovascular system; the trachea; the sinus cavity, the female reproductive system; the abdominal cavity; or any other part of the human body to be explored via a natural or artificial approach.

In general manner, a medical endoscope for single use or with a single patient includes a control handle that, by means of an attachment system, is temporarily attached to a consumable medical instrument that is generally in the form of a tube. Such an endoscope generally has an optical viewing system making it possible to illuminate and to examine the organ, cavity, or passage in the human body. In conventional manner, a medical endoscope also has a system for enabling the distal end of the medical instrument to be folded or guided in order to steer the tube.

In the state of the art, various endoscope solutions are known in which a tubular instrument is detachable from a handle. For example, WO 2008/086497 describes an endoscope having a support handle on which a detachable instrument is designed to be mounted temporarily, the proximal end of its insertion tube being provided with a connection casing with a toothed wheel projecting from its end and suitable for co-operating with an actuation gearwheel equipping the handle. Attaching the detachable instrument to the handle provides the mechanical connection between the toothed wheel and the gearwheel. The toothed wheel of the detachable instrument makes it possible to act on cables fastened to the free end of the insertion tube so as to enable it to be steered. The connection casing also has an optical portion making it possible to co-operate with a complementary optical portion presented by the handle to form a viewing system when the medical instrument is attached to the handle.

In numerous applications, it appears advantageous to bring one or more pieces of equipment to the distal portion of the insertion tube, such equipment being adapted to perform various functions, such as feeding in a fluid, sucking out a fluid, feeding in instruments, taking samples, or performing surgical operations. In order to satisfy such a need, U.S. Pat. No. 6,017,322 proposes to implement one or more tubular ducts extending along the insertion tube and each provided at its proximal end with a releasable mounting connector for mounting on the handle. That mounting connector is designed to be connected to a system for feeding in or sucking out fluids. That solution offers the advantage that the fluid flow circuit is independent of the handle so that the handle is not soiled by the fluid coming from the patient. However, a drawback with that endoscope relates to the difficulty of connecting the handle to the tubular ducts and the system for folding the medical instrument, and to the time that requires. In addition, that endoscope does not incorporate any technical solution for controlling closure of the tubular ducts, simultaneously or otherwise, and therefore does not make it possible to keep a circuit sterile until it is used.

In the state of the art, various systems are also known that make it possible to control the irrigation of a surgical site. For example, U.S. Pat. No. 5,484,402 and U.S. Pat. No. 6,364,853 describe irrigation and suction systems designed to be used in association with an endoscope. Such a system includes, in particular, a graspable handle formed by assembling together two half-shells inside which a suction tube and an injection tube are mounted, which tubes are deformable via a mechanism actuated manually for controlling opening and closing of the tubes. Such a system is suitable for controlling the irrigation of a surgical site without however performing the functions of an endoscope. Furthermore, such a system is not designed to have either a re-usable portion that is not soiled while it is being used, or a consumable portion suitable for being removed easily from the reusable portion.

An object of the present invention is thus to remedy the drawbacks of the prior art by proposing a novel medical endoscope designed for single use, or for a single patient, and including a consumable medical instrument that is temporarily attached to a control handle, this endoscope being designed to make it simple and quick to mount firstly the system for folding or guiding the head of the medical instrument, and secondly at least one fluid flow circuit, that can be controlled simply and effectively to close off, making it possible in particular to keep said flow circuit sterile even after it has been attached to the control handle.

To achieve such an object, the medical endoscope of the invention includes a control handle provided with a control mechanism and that, by means of an attachment system, is temporarily attached to a consumable medical instrument including:

at least one flow circuit for a fluid, a portion of which circuit extends along an insertion tube, the fluid circuit including a connector fitting accessible independently from the handle; and an actuation system for actuating the head of the insertion tube, which actuation system is driven by the control mechanism after the handle and the consumable medical instrument have been attached together.

In accordance with the invention, the control handle and the consumable medical instrument respectively have a first portion and a second portion of a closure device, which portions co-operate with each other in the attached position to close off at least one fluid flow circuit in controlled manner.

The endoscope of the invention may also have any one of the following characteristics, or any combination of them:

the controlled closure device firstly ensures that a flow circuit is not closed off prior to attachment, and secondly that the flow circuit is closed off automatically after attachment;

the first portion and the second portion are carried respectively by the consumable medical instrument and by the handle, one of the portions comprising a closure member while the other portion comprises a control member for controlling the closure member and co-operating with said closure member after the handle and the consumable medical instrument have been attached together;

the first portion is formed by a deformable portion of the flow circuit, while the second portion comprises a clamp acting after attachment and on the deformable portion of the flow circuit, and caused to move by a control button for controlling closure of said circuit.

the clamp acts on at least two fluid flow circuits to open one and to close the other simultaneously, and vice versa;

the controlled closure device includes masking means for masking the clamp during the attachment, enabling it to be positioned without deforming the deformable portion, these masking means no longer acting on the clamp after attachment so that the clamp can close off the flow circuit;

a locking member for locking the attachment between the consumable medical instrument and the handle co-operates automatically with a blocking member at the end of the stroke over which the support and the consumable medical instrument are brought together;

the blocking member is driven by the control button of the clamp in order to unlock the locking member causing the consumable medical instrument and the handle to be detached;

the actuation system includes at least one pulley provided with a male or female coupling member designed to co-operate, after attachment, respectively with a respectively female or male coupling member of the control mechanism equipping the handle;

the actuation system includes at least one pair of pulleys mounted on a common axis;

each male or female coupling member equipping the control handle is provided with a control lever; and the medical instrument includes a vision system suitable for illuminating and for returning an image from a portion of the insertion tube that is remote from the proximal portion.

Various other characteristics appear from the following description given with reference to the accompanying drawings which show embodiments of the invention by way of non-limiting example, and in which.

Figure 1:
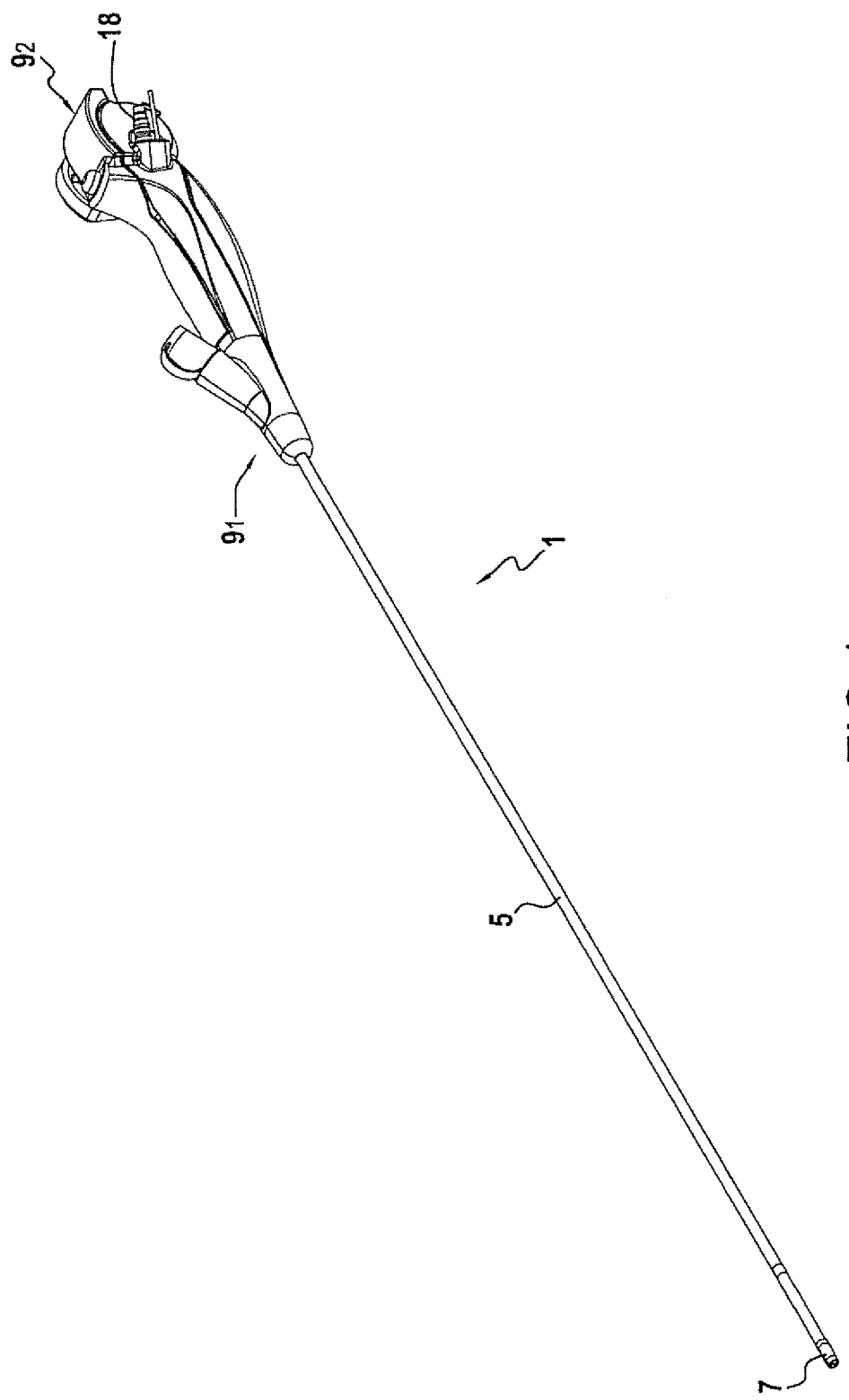
FIG. 1 is a perspective view of a medical endoscope of the invention.
Figure 5:
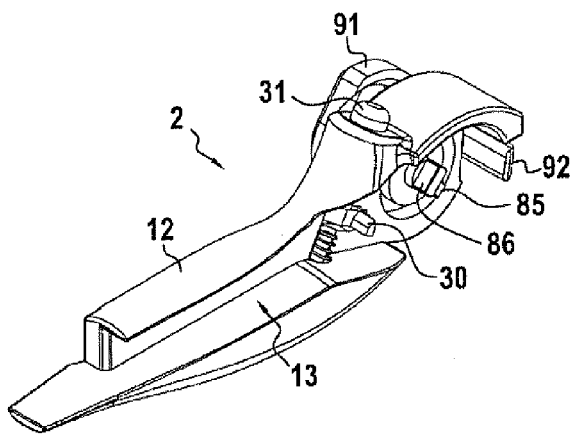
FIG. 5 is a perspective view showing the inside of the handle of the medical endoscope of the invention.
Figure 6:
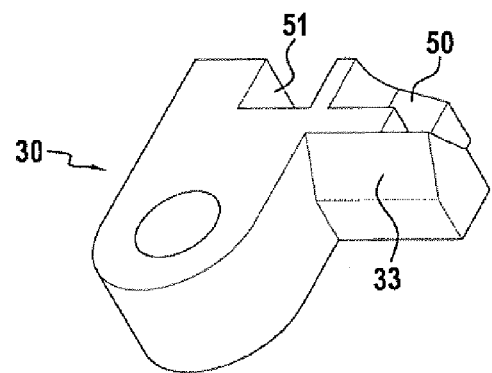
FIG. 6 is a perspective view showing the clamp used by the endoscope of the invention.

As can be seen more precisely in FIGS. 1 and 5, the invention relates to a medical endoscope 1 having an actuation support 2 such as a control handle to which a consumable medical instrument 3 is attached temporarily. This consumable medical instrument 3, which comes into contact with human tissue or organs, is essentially for single use, or to be used more than once on the same patient, or else may be reusable after being decontaminated, disinfected, or indeed sterilized.

Figure 2:
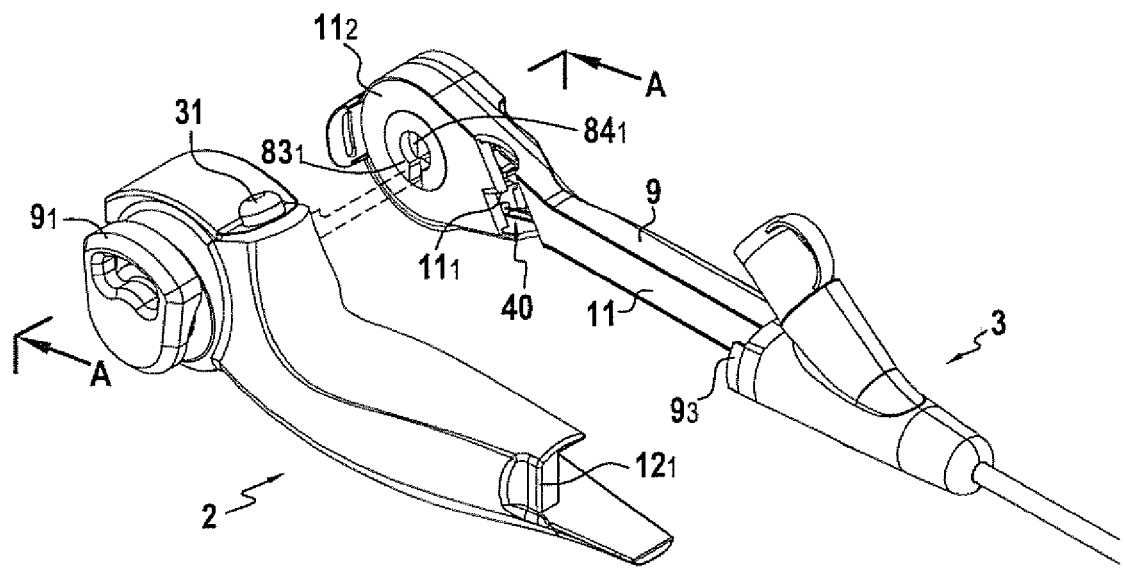
FIG. 2 is a perspective view of a medical endoscope of the invention with the consumable medical instrument detached from the handle.

The consumable medical instrument 3 is designed to be attached temporarily to the support 2 by means of an attachment system 4. In an advantageous embodiment, the attachment system 4 is of the snap-fastening type, as explained in the description below. The attachment system 4 is adapted to procure rapidly a temporary connection that is at least mechanical while also offering the advantage of enabling the consumable medical instrument 3 to be detached easily from the support 2. The attachment system 4 thus procures a releasable connection between the control handle 2 and the consumable medical instrument 3, making it possible to reuse the control handle 2 with other consumable medical instruments 3. FIG. 1 shows the endoscope in the attached position while FIG. 2 shows the consumable medical instrument 3 detached from the support 2. The position of the endoscope that is shown in FIG. 2 is referred to in the description below as the "detached position".

In conventional manner, the consumable medical instrument 3 includes an outer insertion tube 5 that may be of length and of flexibility that are of various magnitudes and that is designed to be inserted into a natural or artificial access approach with a view to performing various operations or functions for therapeutic, surgical, or diagnostic purposes. For example, the insertion tube 5 has a distal portion 7 forming the head of the endoscope 1. The insertion tube 5 also has a proximal portion 8 opposite from the distal portion 7 and extending proud from the distal end $9_1$ of a casing 9 forming the main body for mounting on the support 2.

This casing 9 is in the form of an elongate body that is substantially of channel section, the open face of which is closed by a lid 11. Similarly, the support 2 is in the form of an elongate body 12 that is substantially of channel section, the open face 13 being designed to come into register with the lid 11 when the support 2 is attached to the consumable medical instrument 3. It should be considered that, in the attached position, the support 2 and the casing 9 of the consumable medical instrument 3 co-operate to form a graspable handle making it easy to take hold of the endoscope. In other words, the body 12 and the casing 9 form respective half-shells that, after attachment, give the handle its final shape.

Figure 3:
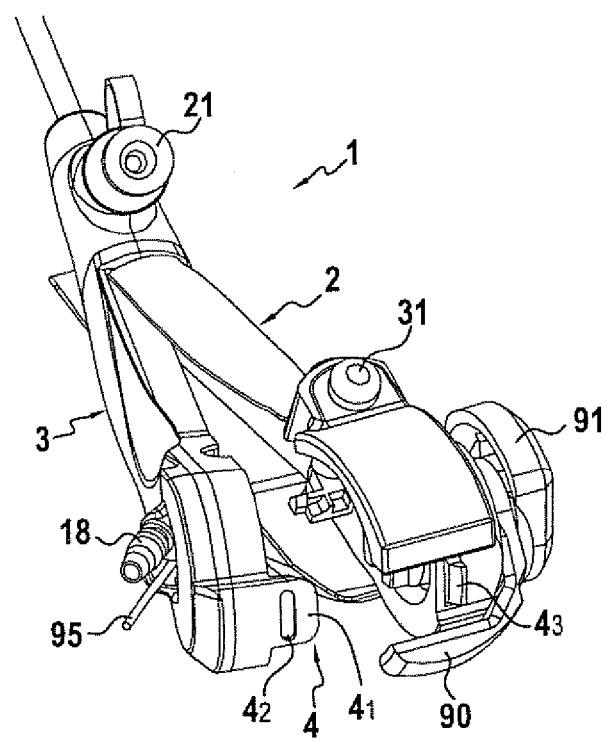
FIG. 3 is a perspective view showing how the consumable medical instrument is attached to the handle.
Figure 4:
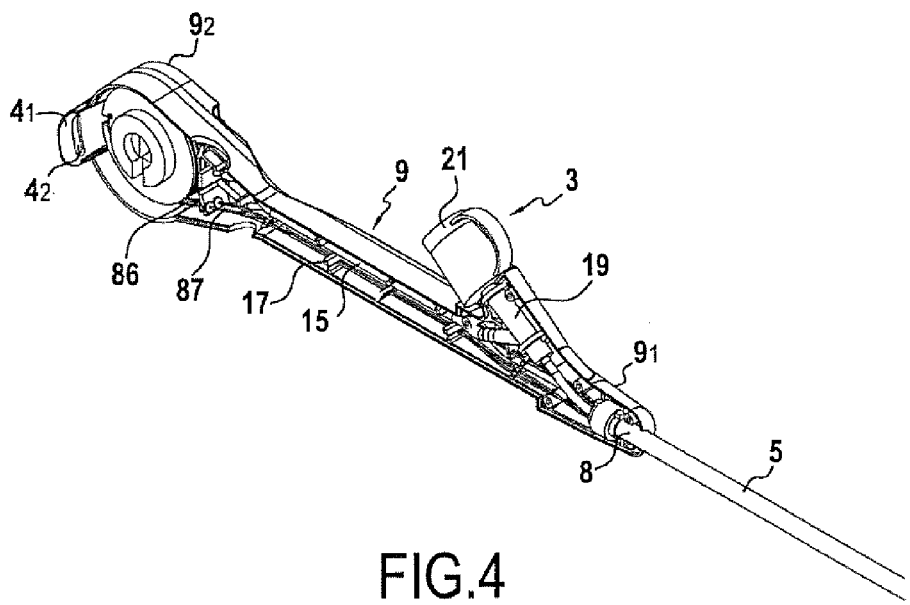
FIG. 4 is a perspective view showing the inside of the consumable medical instrument of the medical endoscope of the invention.

The consumable medical instrument 3 has at least one fluid flow circuit 15 extending along the insertion tube 5 between the distal end 7 and the proximal end 8 (FIG. 4). In the example shown, the flow circuit 15 comprises a tubular pipe extending inside the insertion tube 5 to its distal portion 7. This tubular pipe 15 comes out of the insertion tube 5 by being extended inside the casing 9. Advantageously, the tubular pipe 15 is held in a stationary position inside the casing by catches 17 extending inside the casing. The tubular pipe 15 comes out at the proximal portion $9_2$ of the casing that is opposite from the distal portion $9_1$ (FIG. 3). Outside the casing 9, the tubular pipe 15 is provided with a connector fitting 18 for connecting to a suction source or to a fluid feed source.

In an advantageous variant embodiment, the flow circuit 15 includes a branch 19 so that the circuit forms a Y-shape at the branch. In the example shown, the branch 19 is formed at the distal end $9_1$ of the casing 9 which thus constitutes a triangular-shaped tip. This branch 19 serves to pass various tools that are to be brought to the distal portion 7 of the insertion tube 5. Said branch 19 is optionally closed by a stopper 21.

In accordance with the invention, the control handle and the consumable medical instrument 3 respectively have a first portion and a second portion of a closure device, which portions co-operate with each other in the attached position to close off at least the flow circuit 15 in controlled manner.

Figure 7:
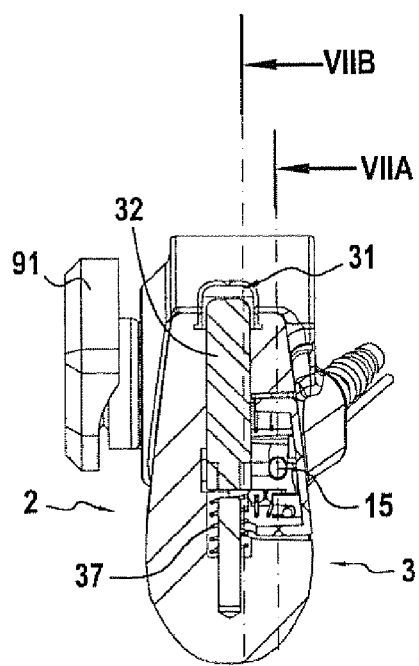
FIG. 7 is a cross-section view substantially on the lines A-A of FIG. 2, showing the endoscope in a position prior to attachment.
Figure 7A:
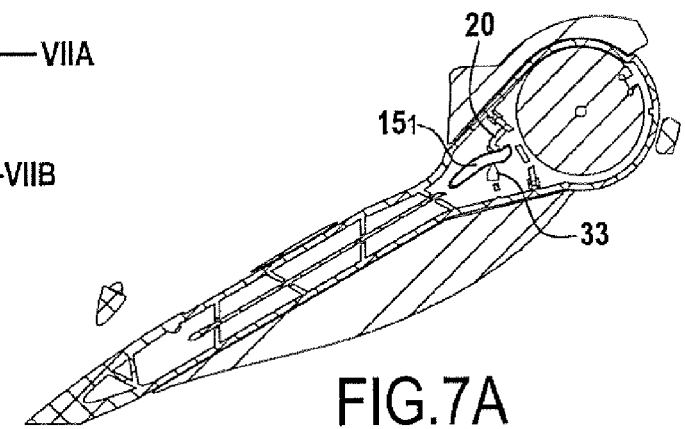
FIGS. 7A and 7B are longitudinal section views taken respectively substantially on line VII-A and substantially on line VII-B of FIG. 7.
Figure 7B:
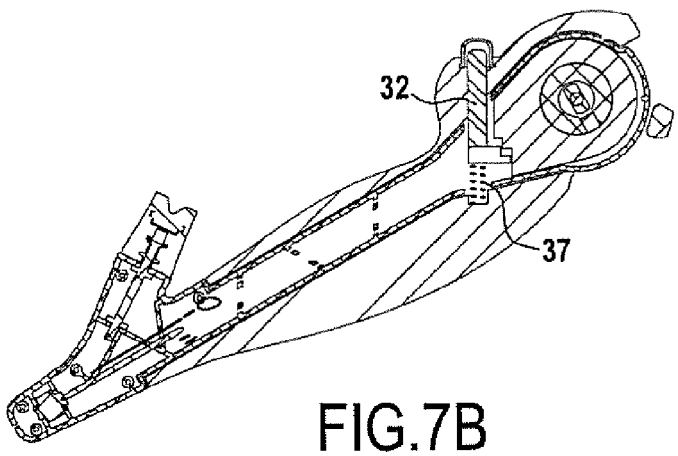

In the embodiment shown, the first portion equips the consumable medical instrument 3 and is formed by a deformable portion $15_1$ of the flow circuit 15 (FIGS. 7, 7A). Advantageously, this deformable portion $15_1$ is held in place, inside the casing 9, by positioning abutments 20.

Figure 8:
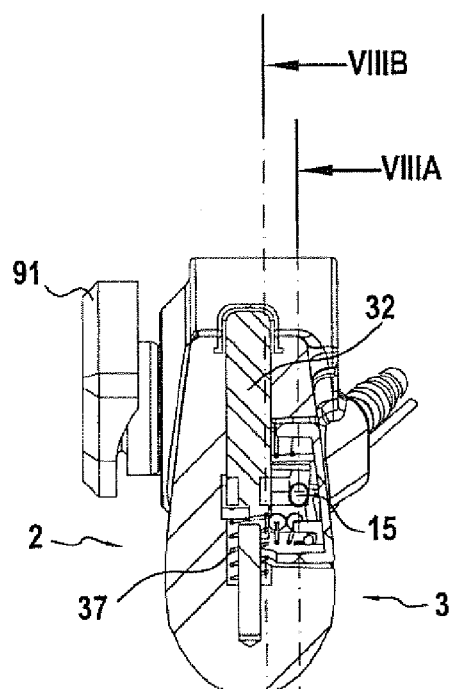
FIG. 8 is a cross-section view taken substantially on line A of FIG. 2, and showing the endoscope in the attached position.
Figure 8A:
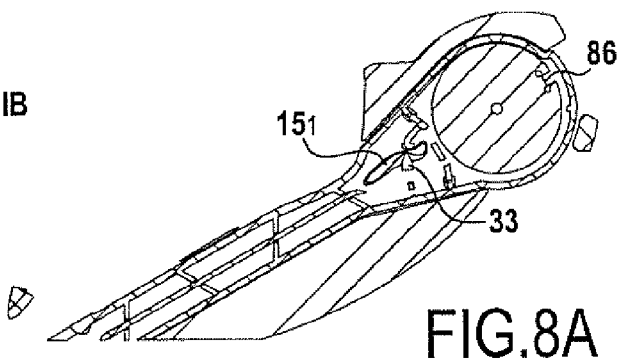
FIGS. 8A and 8B are longitudinal section views taken respectively on line VIII-A and on line VIII-B of FIG. 8.

The second portion of the controlled closure device is carried by the control support 2 and has a closure member or a clamp 30 acting, after attachment, on the deformable portion $15_1$ of the circuit. This clamp 30 is caused to move via a control button 31 making it possible to control closure of the circuit 15. In the example shown, the clamp 30 is mounted to move linearly, substantially in a direction transverse to the deformable portion $15_1$ of the fluid circuit in order to enable it to be nipped (FIGS. 7A, 8A). To this end, the clamp 30 has a beveled projecting portion 33 adapted to act on the wall of the circuit $15_1$. Advantageously, the deformable portion of the circuit 15 that is opposite from the portion on which the projecting portion 33 presses finds itself bearing against an abutment 20 in order to guarantee that the circuit 15 is closed in controlled manner.

Figure 8B:
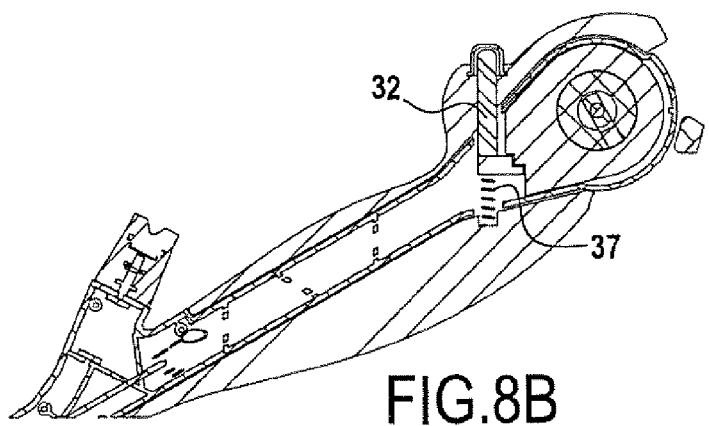
Figure 9:
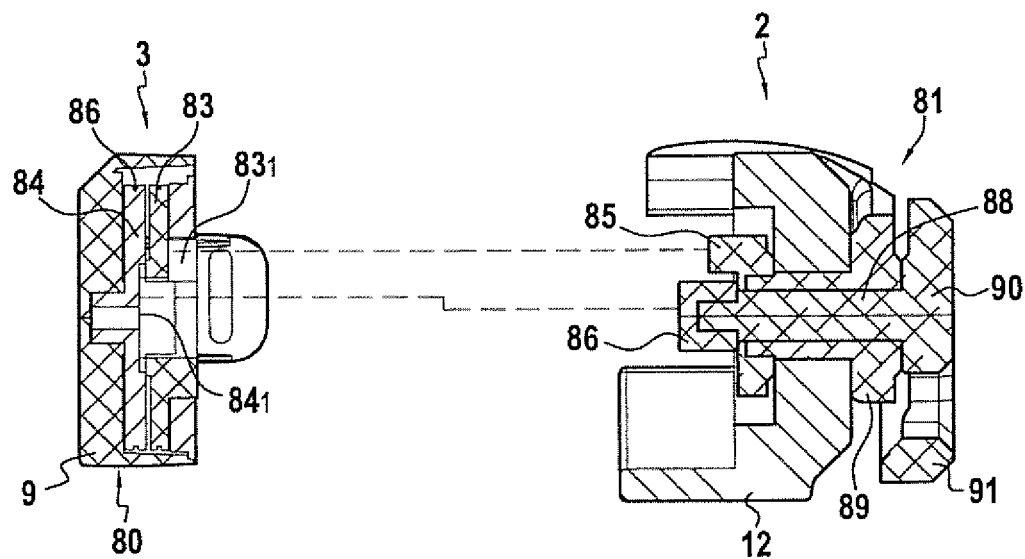
FIG. 9 is an embodiment of the actuation system for actuating the insertion tube.

As can be seen more precisely in FIG. 7, the clamp 30 is carried by a slidably mounted pin 32 that projects from the support 2 to form the control button 31. The pin 32 is biased by a spring 37 making it possible, in the absence of any pressing force on the control button 31, to place the clamp 30 in a fully-closed position in which it fully closes the circuit 15, i.e. in which the projecting portion 33 nips the deformable portion $15_1$ of the circuit (FIGS. 8, 8A, 8B).

As can be seen more clearly in FIG. 2, it should be noted that the lid 11 is provided with an opening 40 enabling the clamp 30 to pass through during the attachment operation, and to be positioned relative to the deformable portion $15_1$ of the circuit.

In accordance with an advantageous implementation characteristic, the controlled closure device has masking means 50 for masking the clamp 30 during attachment, which means enable the clamp and the circuit 15 to co-operate without deforming the deformable portion $15_1$ of the circuit. The masking means 50 are formed by a ramp provided on the clamp 30 and against which the edge $11_1$ of an auxiliary lid $11_2$ comes to bear during the attachment operation, which auxiliary lid comes to lie in the same plane as the lid 11. The edge $11_1$ of the auxiliary lid $11_2$ defines the opening 40 in part. Thus, while the support 2 and the consumable medical instrument 3 are being brought together, the edge $11_1$ of the auxiliary lid $11_2$ comes to bear against the ramp 50, thereby causing the clamp 30 to slide towards its position in which it does not close off the circuit. During this movement, the spring 37 is compressed. The deformable portion $15_1$ of the circuit then comes to lie in the space vacated in this way by the clamp 30. Thus, the consumable medical instrument 3 and the support 2 being brought together results in almost no deformation of the deformable portion $15_1$ of the circuit. At the end of the bringing-together stroke, the edge $11_1$ of the auxiliary lid $11_2$ escapes from the ramp 50 so as to come into a recess 51 provided for receiving it in the clamp 30. In this final attachment position, the clamp 30 is no longer stressed by the edge $11_1$ of the auxiliary lid $11_2$ so that, under the action of the compression spring 37, the clamp 30 slides freely to come to take up its nipping position or its position of partial or total closure of the deformable portion $15_1$ of the circuit (FIGS. 8, 8A, 8B).

It follows from the above description that the controlled closure device ensures that the circuit 15 is not closed off before it is attached to the support 2. Thus, the circuit 15 is not deformed throughout the entire time for which the consumable medical instrument 3 is stored. In addition, attaching the consumable medical instrument 3 to the support results in the circuit 15 being automatically closed off by the clamp 30, thereby making it possible to isolate the circuit 15 from the outside. Bringing the support 2 and the consumable medical instrument 3 together enables these parts to be attached together automatically by operation of the attachment system 4 of the snap-fastening type.

In the example described, the clamp 30 acts on one flow circuit 15 only. Naturally, the clamp 30 can act simultaneously on a plurality of flow circuits 15. For example, the clamp 30 may be arranged to close or to open the flow circuits 15 simultaneously, or to open at least one flow circuit 15 and, simultaneously, to close at least one other flow circuit 15, and vice versa.

In the embodiment shown, the attachment system 4 is provided with a snap-fastening tongue $4_1$ extending proud, e.g. from the proximal end $9_2$ of the casing. This tongue $4_1$ is provided with an orifice $4_2$ designed to engage over a lug $4_3$ carried by the proximal end of the support 2 when the support 2 and the consumable medical instrument 3 are brought together. In addition, at its distal end, the support 2 is provided with a bearing edge $12_1$ coming to engage under a rim or a lip $9_3$ provided on the casing 9. As appears more precisely in FIG. 3, attaching the endoscope 1 consists in engaging the bearing edge $12_1$ of the support 2 beneath the lip $9_3$ on the casing 9, and then in bringing the proximal ends of the casing 9 and of the support 12 together until the tongue $4_1$ is engaged over the snap-fastening lug $4_3$.

In the above description, the attachment system 4 is of the snap-fastening type. Naturally, the attachment system 4 may be of some different type. For example, the attachment system 4 may have fastening hooks or levers ensuring that the control handle 2 and the consumable medical instrument 3 are easy to attach to each other and to detach from each other.

In accordance with an advantageous implementation characteristic, the endoscope 1 of the invention is also provided with a locking member for locking the attachment between the support 2 and the consumable medical element in order to avoid these two parts coming apart in untimely or accidental manner. The locking member is controlled to allow the support 2 and the consumable medical instrument 3 to be detached after use. In the example shown, the attachment is locked by the edge $11_1$ of the auxiliary lid $11_2$ engaging in the recess 51 of the clamp 30. As explained above, the locking of the attachment between the support 2 and the consumable medical instrument 3 is achieved automatically during the operation of attaching together the support 2 and the consumable medical instrument 3 because the clamp 30 comes to take up its blocking position in which it blocks the edge $11_1$ under the action of the spring 37. Thus, the locking edge $11_1$ co-operates automatically with the blocking recess 51 at the end of the mutual stroke of the support 2 and of the consumable medical instrument 3. Unlocking is obtained firstly by actuating the control button 31, leading to the edge $11_1$ being disengaged from the blocking recess 51, and secondly by the snap-fastening tongue $4_1$ unhooking from the lug $4_3$, followed by the support 2 and the consumable medical instrument 3 moving apart at the tongue 4₁. The blocking member 51 (such as the recess) is driven by the control button 31 of the clamp 30 in order to unlock the locking member 11₁ causing the consumable medical instrument and the handle to come apart. This double action thus makes it possible to detach the consumable medical instrument 3 relative to the support 2 in safe and controlled manner.

In a preferred variant embodiment, the medical endoscope 1 also has a mechanism enabling the head 7 of the insertion tube 5 to be actuated. The consumable medical instrument 3 thus has a system 80 for actuating the head 7 of the insertion tube 5. The actuating system is driven by a control mechanism 81 equipping the support 2. In a preferred variant embodiment, the actuating system 80 has at least a first pulley and, in the example shown, a first pulley 83 and a second pulley 84, each of which is provided with a male or female coupling member 83₁, 84₁ designed to co-operate with a male or female coupling member 85, 86 equipping the control support 3. The two pulleys 83, 84 are advantageously mounted on a common axis inside the casing 9. Each pulley 83, 84 is provided on its transverse face with a male or female coupling member 83₁, 84₁. The end of at least one cable 86 mounted inside the casing 9 is fastened to the periphery of each pulley 83, 84. In conventional manner, and as appears precisely from FIG. 4, each cable 86 is mounted inside a sheath 87 mounted inside the casing 9 and passing through the inside of the insertion tube 5. The end(s) of the cable(s) 86 is/are connected to the head 7 of the tube 5.

Thus, for example, one of the pulleys 83, 84 controls the left-right movement of the head 7, while the other pulley controls the up-down movement. These pulleys 83, 84 are designed to be connected mechanically to the male and female coupling members 85, 86 that are driven in rotation by any manual or motor-driven means. In the example shown, the male and female coupling members 85, 86 are provided on disks 88, 89 mounted coaxially one inside the other in the body 12. Each of these disks 88, 89 is provided with a control lever 90, making it possible to cause the male and female coupling members 85, 86 to move in rotation, and thereby causing the pulleys 83, 84 to move in rotation. In the example shown, each control lever 90, 91 is of the rotary type. One of the levers extends laterally relative to the casing 9 while the other lever extends behind the distal portion of the casing 9. Naturally, the control levers 90, 91 may be of some different type, e.g. linear.

It appears from the above description that attaching together the control handle 2 and the consumable medical instrument 3 causes the control mechanism 81 equipping the handle 2 to co-operate with the actuation system 80 that is part of the consumable medical instrument 3. Mounting a consumable medical instrument 3 on the control handle 5 makes it possible to activate firstly the control function for controlling closure/opening of the fluid flow circuit 15 and secondly the actuation function for actuating the head of the insertion tube 5.

The endoscope 1 of the invention also includes a vision system 95 suitable for illuminating and for returning an image from a portion of the insertion tube 5 that is remote from the proximal portion of the insertion tube 5. For example, the vision system 95 is suitable for illuminating and for returning an image from the distal portion 7 of the insertion tube 5. The consumable medical instrument 3 thus includes vision means mounted inside the casing 9 and penetrating through the inside of the tube 5 to the head 7 of the insertion tube 5.

The invention is not limited to the examples described and shown since various modifications may be made to them without going beyond the ambit of the invention.

The invention claimed is:

1. A medical endoscope including a control handle provided with a control mechanism and that, by means of an attachment system, is temporarily attached to a consumable medical instrument including: at least one flow circuit for a fluid, a portion of which circuit extends along an insertion tube, the fluid circuit including a connector fitting accessible independently from the handle; and an actuation system for actuating the head of the insertion tube, which actuation system is driven by the control mechanism after the handle and the consumable medical instrument have been attached together; said medical endoscope being characterized in that the control handle and the consumable medical instrument, respectively, have a first portion and a second portion of a closure device, which portions co-operate with each other in the attached position to close off at least one fluid flow circuit in a controlled manner;

wherein the first portion is formed by a deformable portion of the flow circuit that is not closed off prior to attachment, between the control handle and the consumable medical instrument; and the second portion comprises a clamp, acting after attachment and on the deformable portion of the flow circuit in order to close off the flow circuit automatically, and caused to move by a control button for controlling closure of said circuit; wherein the clamp is carried by a slidably mounted pin that projects from the support to form a control button, making it possible to control closure of the circuit, the pin being biased by a spring, making it possible, in the absence of any pressing form of the control button, to place the clamp in a fully closed position in which the clamp fully closes the circuit.

2. A medical endoscope according to claim 1, characterized in that the first portion and the second portion are carried respectively by the consumable medical instrument and by the handle, one of the portions comprising a closure member, while the other portion comprises a control member for controlling the closure member and co-operating with said closure member after the handle and the consumable medical instrument have been attached together.

3. A medical endoscope according to claim 1, characterized in that the controlled closure device includes masking means for masking the clamp during the attachment, enabling it to be positioned without deforming the deformable portion, these masking means no longer acting on the clamp after attachment so that the clamp can close off the flow circuit.

4. A medical endoscope according to claim 1, characterized in that it includes a locking member for locking an attachment between the consumable medical instrument and the handle, which locking member co-operates automatically with a blocking member at the end of a stroke over which the support and the consumable medical instrument are brought together.

5. A medical endoscope according to claim 4, characterized in that the blocking member is driven by the control button of the clamp in order to unlock the locking member causing the consumable medical instrument and the handle to be detached.

6. A medical endoscope according to claim 4, characterized in that the actuation system includes at least one pair of pulleys mounted on a common axis.

7. A medical endoscope according to claim 1, characterized in that the actuation system includes at least one pulley provided with a male or female coupling member designed to co-operate, after attachment, respectively with a female or male coupling member of the control mechanism equipping the handle.

8. A medical endoscope according to claim 7, characterized in that each male or female coupling member equipping the control handle is provided with a control lever.

9. A medical endoscope according to claim 1, characterized in that the medical instrument includes a vision system suitable for illuminating and for returning an image from a portion of the insertion tube that is remote from the proximal portion.

\* \* \* \* \*